United States Patent [19]
Kunig

[11] Patent Number: 5,025,795
[45] Date of Patent: *Jun. 25, 1991

[54] NON-INVASIVE CARDIAC PERFORMANCE MONITORING DEVICE AND METHOD

[76] Inventor: Horst E. Kunig, R.D. #1, Box 577, Saltsburg, Pa. 15681

[*] Notice: The portion of the term of this patent subsequent to Aug. 8, 2006 has been disclaimed.

[21] Appl. No.: 373,229

[22] Filed: Jun. 28, 1989

[51] Int. Cl.$^5$ .......................................... A61B 5/0452
[52] U.S. Cl. ................................... 128/713; 128/696; 128/704; 128/707
[58] Field of Search ............... 128/704, 713, 708, 700, 128/696, 671, 716, 718

[56] References Cited

U.S. PATENT DOCUMENTS

| | | | |
|---|---|---|---|
| 3,554,187 | 1/1971 | Glassner | 128/706 |
| 3,572,321 | 3/1971 | Bloomfield et al. | 128/704 |
| 4,622,980 | 11/1986 | Kunig | 128/704 |
| 4,754,762 | 7/1988 | Stuchl | 128/704 |
| 4,854,327 | 8/1989 | Kunig | 128/704 |

FOREIGN PATENT DOCUMENTS 0738601  6/1980  U.S.S.R. .............................. 128/708

Primary Examiner—William E. Kamm
Assistant Examiner—Kennedy J. Schaetzle
Attorney, Agent, or Firm—Clifford A. Poff

[57] ABSTRACT

A non-invasive cardiac monitoring device for calculating the cardiac performance parameters of heartbeat, stroke volume, and cardiac output for an individual. The device receives a plurality of electrocardiogram waveform signals from the individual and selects the R-wave component having the maximum value of the electrocardiogram waveform signals and the T-wave component having the maximum value of the electrocardiogram waveforms. From these values, the stroke volume of the individual and the cardiac output of the individual may be calculated according to the equation: Stroke Volume = $6 \times R(max.)/T(max.) + 26.0$. The periodicity of subsequent electrocardiogram waveforms are utilized to calculate the cardiac performance of the individual.

13 Claims, 6 Drawing Sheets

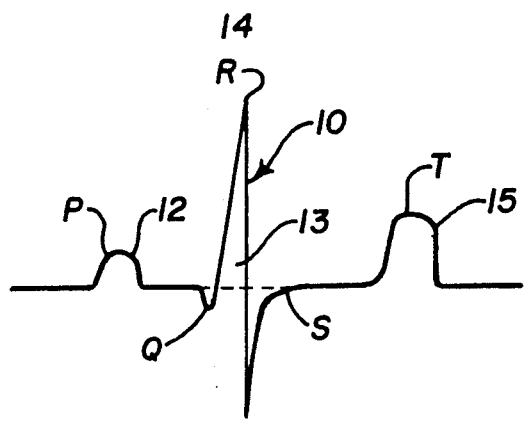
FIG. IA
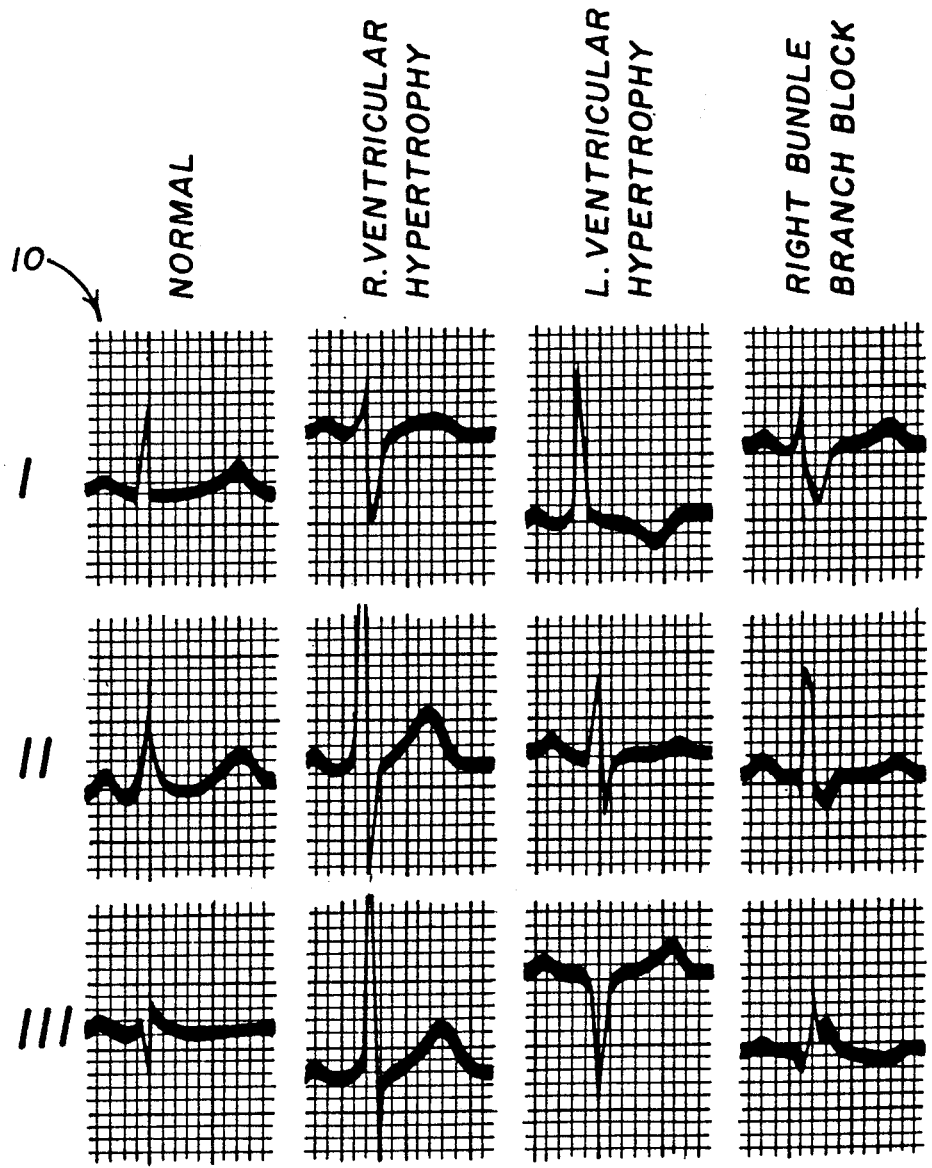
FIG. IB

OXYGEN EXERCISE

EXERCISE

NON-INVASIVE CARDIAC PERFORMANCE MONITORING DEVICE AND METHOD

BACKGROUND OF THE INVENTION

1. Field of the Invention

The present invention relates generally to a non-invasive cardiac monitor and, more particularly, to a method and apparatus for determining the cardiac performance of an individual by selecting a R-wave amplitude and a T-wave amplitude having greatest magnitudes from a plurality of electrocardiogram wave forms for determining a stroke volume value which can be on a continuous basis.

2. Description of the Prior Art

Various means have been developed in order to quantify the cardiac performance of an individual. Two parameters are commonly obtained to quantitatively measure the individual's cardiac performance.

The first of the parameters, referred to as stroke volume, is defined as the volume of blood pumped by the individual's heart in one heartbeat. The second parameter, referred to as cardiac output, is defined as the volume of blood pumped by the individual's heart in one minute. Cardiac output, thus, is the sum of the stroke volume over sixty seconds, and, may be derived from taking the sum of an individual's stroke volume over sixty seconds.

Presently, several different invasive methods are utilized in order to obtain values for these parameters. One such method, the Fick method, determines a value for the stroke volume by determining oxygen consumption of the individual and detecting changes in an individual's arterio-venous oxygen concentration levels. A second invasive method, the thermodilution, determines a value of cardiac output through an analysis of the changes of the temperature of a cold bolus injected into the individual's circulatory system. The cold bolus, having a temperature less than that of blood, causes a temporary decrease in the temperature of the individual's heart as the bolus enters the heart chambers. Once the bolus is pumped from the heart chambers and replaced by the higher temperature blood, the temperature of the heart recovers. By measuring the amount of time required for the heart temperature to recover, the volume of blood pumped during this period of time may be calculated, such calculated value being extrapolated to produce a value of the cardiac output in sixty seconds. Instead of a cold bolus, a dye maybe injected and the stroke volume is determined from the dilution of the dye.

The use of the invasive methods of determining the stroke volume and/or cardiac output of an individual are potentially dangerous, and are frequently unable to be performed as catheters must be inserted into the heart or other parts of the circulatory system to obtain the required information. Additionally, both the Fick method and the thermodilution and dye methods, in actuality, measure the average stroke volume and/or cardiac output of an individual by measuring the amount of blood circulated over a specific period of time and dividing the measured volume by the number of heartbeats of the individual's heart during that period of time. As is inherent in any average value, the average may differ substantially from that of a single value. In this instance, the actual stroke volume associated with a single heartbeat of the individual may differ from the average as the individual's stroke volume may fluctuate considerably from heartbeat to heartbeat, depending upon the activity performed by the individual.

Three non-invasive methods of determining stroke volume are alternatively used. The first such method, the Doppler-ultrasound method, determines a value for the stroke volume of an individual by calculating the Doppler effect upon an ultra-high frequency sound wave reflected from moving blood cells. The second method, the bioimpedance method, calculates the value for stroke volume of an individual by modulating a d.c. current by a measured blood pressure wave. The third method, the echocardiography method, calculates a value for the stroke volume based upon measurements of the size of the heart chamber of the individual.

While the Doppler-ultrasound and bioimpedance methods of determining stroke volume are non-invasive procedures and incur little risk to the patient, the methods cannot be utilized when performing certain medical procedures, such as open heart surgery. For instance, in order to perform the Doppler-ultrasound method, sensors must be positioned, and often repositioned, in the esophageal and sternal areas of the individual, and in order to perform the bioimpedance method, eight electrodes must be positioned in precise locations. And the third non-invasive method, the echocardiography method, is of limited usefulness as only intermittent visualization of the heart chamber of the individual is possible. Therefore, the echocardiography method is also precluded for use during certain medical procedures, such as open heart surgery.

Most recently, electrocardiogram waveform changes were utilized to determine cardiac functions. One such method is disclosed in my earlier U.S. Pat. No. 4,622,980. In this disclosure, an electrocardiogram waveform is separated into its components parts, the center spike or R-wave, the left-side sinusoidal P-wave, and the right-side sinusoidal T-wave. The electrocardiogram waveform is quantified by measuring the R-wave amplitude and the T-wave amplitude, and then calculating the ratio of the R-wave amplitude to the T-wave amplitude. The ratio is first calculated when the individual is at rest. The same ratio is then calculated subsequent to the application of a stress to the individual's cardiovascular system. The pre-stress ratio is then compared with the ratio calculated subsequent to the application of the stress. This new value is referred to as the stress index, S, and may be utilized to relate stressful events in terms of electrocardiogram waveform changes on a numerical scale.

A second method is disclosed in U.S. Pat. No. 3,572,321, to Bloomfield. In this disclosure, the R-wave amplitude and T-wave amplitude are measured, and a ratio of the two values is calculated. If the ratio is less than a certain value, a cardiac insufficiency is indicated. However, a typical electrocardiogram consists of numerous different waveforms, with a separate waveform corresponding to leads of twelve different electrodes attached at different locations on an individual's body. Because the magnitude of the ratio is dependent upon which waveform is selected, the indication of cardiac sufficiency or insufficiency is dependent upon which waveform is selected. The indication of cardiac sufficiency or insufficiency is then dependent, at least in part, upon which waveforms is selected. This method is claimed to have utility as a quick indicator of cardiac performance during mass screening procedures.

SUMMARY OF THE PRESENT INVENTION

It is therefore the object of the present invention to provide a method and apparatus for quantitatively and noninvasively determining pumping cardiac performance of an individual.

According to the present invention there is provided a cardiac monitoring device for determining cardiac pumping performance of an individual, the cardiac monitoring device comprising means for generating a plurality of electrocardiogram signals indicative of a plurality electrocardiogram waveforms; means for detecting the amplitude of a R-wave electrocardiogram component having the greatest amplitude from the plurality of the electrocardiogram signals; means for detecting the amplitude of a T-wave electrocardiogram component having the greatest amplitude from the plurality of electrocardiogram signals; means responsive to each of the means for detecting for producing a stroke volume signal which is a function of the ratio of the greatest amplitude of the R-wave component to the greatest amplitude of the T-wave component; and means for displaying values of the stroke volume signal.

The present invention provides a method to diagnose cardiac performance of an individual, the method including the steps of: using electrocardiogram sensors on the individual for producing a plurality of electrocardiogram signals corresponding to electrocardiogram waveforms; selecting a T-wave signal corresponding to the amplitude of the T-wave component having the greatest magnitude from the plurality of electrocardiogram signals; selecting a R-wave signal corresponding to the amplitude of the R-wave component having the greatest magnitude from the plurality of electrocardiogram signals; and producing a stroke volume as a function of the ratio of the signals of the selected R-wave component to the selected T-wave component.

The method and apparatus of the present invention are especially useful to form a monitoring function in a cardiac pulmonary rehabilitation program. The stroke volume signal can be used for controlling the supply of oxygen enriched air to the individual particularly when the cardiac pulmonary rehabilitation program includes periods for physical exercise by the individual.

The cardiac monitoring device and method mentioned hereinabove preferably determines the stroke volume by calculating the stroke volume signal according to the equation:

$$\text{stroke volume} = 6 \cdot R/T + 26.0$$

wherein R/T=the value of the ratio signal generated by the ratio calculating means.

BRIEF DESCRIPTION OF THE DRAWINGS

These features and advantages of the present invention as well as others will be more fully understood when the following description is read in light of the accompanying drawings in which:

FIG. 1A is an enlarged illustration of a typical electrocardiographic waveform;

FIG. 1B comprises a series of electrocardiographic waveforms obtained from each of three different leads showing normal waveforms in relation of a abnormal waveform.

DESCRIPTION OF THE PREFERRED EMBODIMENTS

Figures 2, 3:
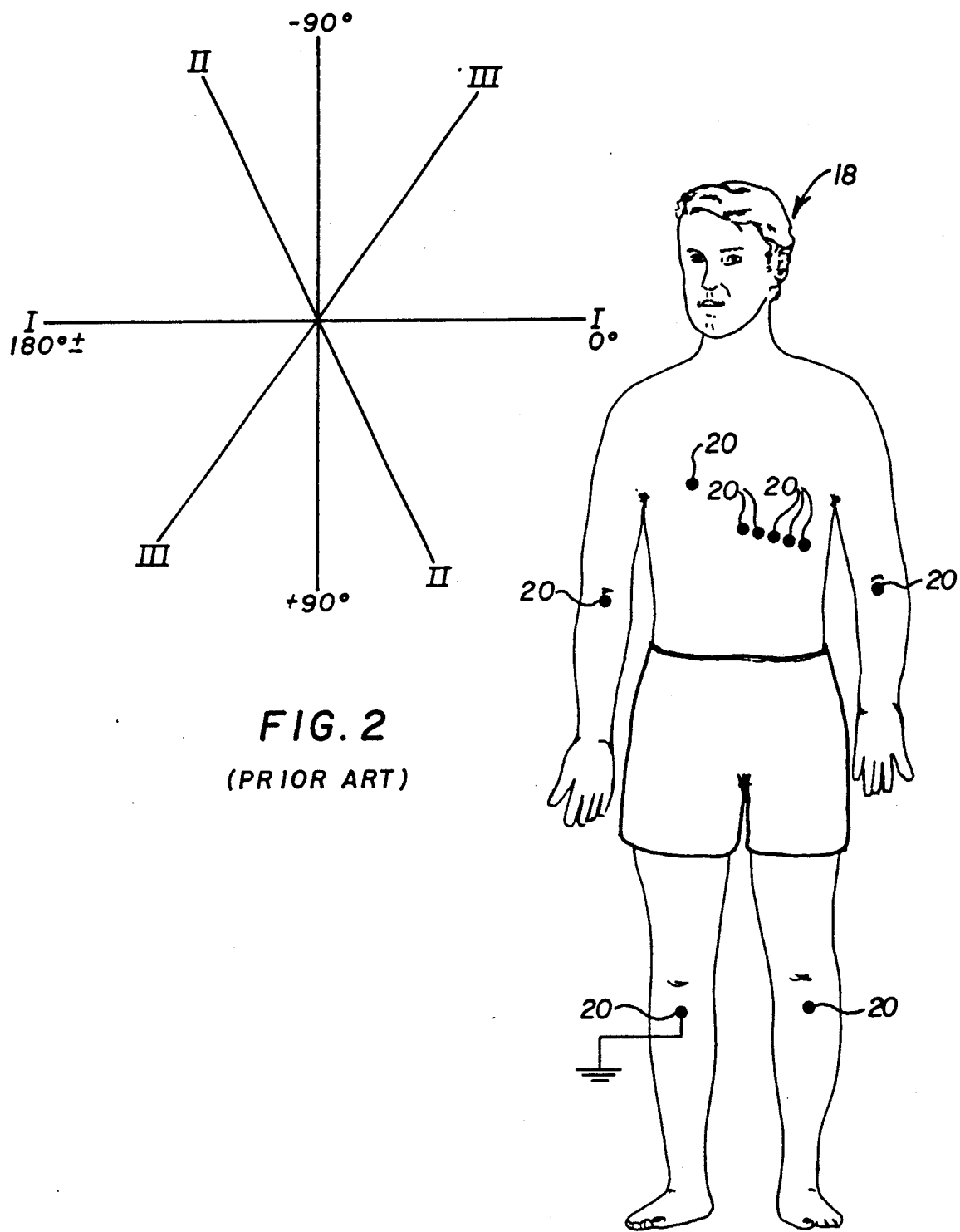
FIG. 2 illustrates the axis system for identifying current vectors between electrode sensors for electrocardiogram leads.
FIG. 3 illustrates the conventional method of placing ten electrode sensors for producing a standard, twelve-lead electrocardiographic waveform signals.

Referring first to FIG. 2A, there is illustrated a typical electrocardiographic waveform 10 which is a graphical representation of depolarization and repolarization of cardiac tissue during normal cardiac functioning. The waveform is a graphically representation of the current changes between two electrode sensors over a time period. This waveform is representative of one heartbeat and is repeated during each heartbeat. The waveform 10 is comprised of a number of component portions, namely a P-wave component 12, QRS-complex wave component 13, R-wave component 14, and T-wave component 15. The P-wave component is actually the graphical representation of depolarization of the atrium, the QRS-complex wave component is the graphical representation of depolarization of the ventricles, and the T-wave component is the graphical representation of repolarization of the cardiac tissue. The waveform illustrates the electrocardiographic waveform of a healthy individual. Cardiac abnormalities are detected by analysis of the electrocardiographic waveforms taken of an individual and discerning the deviations of the waveform from the waveform of a healthy individual.

In FIG. 1B the waveforms appearing in a horizontal row commencing with waveform 10 is illustrative, as labeled normal, a normal waveform of a heartbeat derived using a lead identified by reference numeral 1. A series of waveforms following the waveform labeled normal are illustrative of abnormal conditions which are also labeled above each waveform. Similarly, beneath the first row of waveforms there is a second row of waveforms derived from a lead identified by reference numeral II in which the first waveform is indicative of normal and the series of waveforms in the remaining part of the row are indicative of and which are identified as in the waveforms obtained from reference lead 1. Lastly, a lead identified by reference numeral III illustrates a third series of waveforms beginning with, as labeled, a normal waveform in column number 1 and proceeding with the abnormal waveforms within the series. The abnormalities are identified by legends above each column of waveforms. These waveforms in FIG. 1B are illustrative of the general form, the electrocardiogram waveforms take using leads positioned at different parts of the body and the widely varying characteristics indicative of abnormalities in relation to a normal waveform. The present invention utilizes information derived from the electrocardiogram waveforms for measuring the stroke volume based on a ratio of an R-wave amplitude which is maximum to the T-wave amplitude which is also maximum. The R-wave amplitude is determined by an R-wave vector and similarly the T-wave amplitude is determined from a T-wave vector. These vectors are only in exceptional cases parallel to each other in most individuals, however, in all cases either of right heart or left heart axis deviation both vectors are also sufficiently misaligned. Because of this misalignment two separate sensors must be employed to create one signal with the largest R-wave amplitude and another signal with the largest T-wave amplitude for forming the ratio of R/T and to derive the stroke volume. The electrocardiographic vectors are defined conventionally in a coordinate system.

In FIG. 2, there is shown the axis system frequently utilized in order to describe current vectors formed during cardiac functioning. Currents through cardiac tissue are formed during depolarization and repolarization of the cardiac tissue, a current vector is formed which, by definition, is described by both a magnitude and a direction. The axis system of FIG. 2 is utilized to describe these cardiac current vectors. The origin of the axis system is usually considered to be located at the center of the heart of an individual. A line extending through the origin towards the left arm of the individual is defined to be zero degrees. Positive angles are defined in the clockwise direction relative to the zero degree line, and negative angles are defined by counterclockwise rotation relative to the zero degree line. A vertical line extending upwardly from the origin towards the head of an individual extends at an angle of minus ninety degrees. Normally, a cardiac current vector has a direction of between minus thirty degrees and positive one hundred five degrees. In FIG. 2, the axis corresponding to line I—I is the horizontal axis, the axis corresponding to line II—II passes through sixty and two hundred forty degrees, and the axis corresponding to line III—III passes through minus sixty and plus one hundred twenty degrees.

Turning now to FIG. 3, there is illustrated the standard geometry of positioning a conventional, multi-sensor electrocardiogram sensor set positioned upon an individual 18 wherein a plurality of electrocardiographic electrode sensors 20 have been positioned in a conventional geometry. Pairs of sensors 20 form leads to allow measurement of currents in cardiac tissue and to detect waveforms such as the waveforms of FIGS. 1A and 1B. Each of the electrode sensor pairs forming leads detect cardiac current vectors formed during cardiac functioning. Since the individual sensors of an electrocardiographic sensor set are positioned at different body surface locations of the individual, waveforms having different magnitudes are detected by the leads formed by different pairs of sensors. This can be clearly seen by comparing the waveform derived from leads I, II, and III in FIG. 1B. In particular, the magnitudes of the detected current vectors which form the waveforms are dependent upon the positioning of the electrode sensors. Electrode sensors placed parallel to the R-vector detect the largest voltage. When electrodes are not placed parallel to the R-vector substantially less voltages are measured. Additionally, measurement of the electrocardiographic waveforms from certain electrocardiographic leads may fail to detect deviations from normal waveforms. This can result in a diagnosis of an individual's cardiac performance to be dependent upon which electrocardiographic leads are selected for analysis.

The present invention is based on the relationship between the amplitude of the R-wave component and T-wave component of the electrocardiogram. Specifically, however, a series such as the usual 12 waveforms are analyzed for selecting the R-wave component having a maximum value, and the T-wave component having a maximum value. Upon evaluation of experimental data, it has been shown that there is a linear relationship between the ratio of the maximum R-wave amplitude to the maximum T-wave amplitude and the stroke volume of the individual 18. This relationship between the ratio of R/T and stroke volume was experimentally derived and is defined by the equation:

$$SV = 6*R/T + 26.0$$

wherein SV is the stroke volume of the individual, and R/T is the ratio of the R-wave component with a maximum amplitude to the T-wave component with a maximum amplitude. The invention employs two electrode pairs with one pair creating the wave form having the largest R-wave component and the other pair creating the wave form having the largest T-wave component. Only when the R-wave vector is parallel to the T-wave vector which is seldom the case are the maximum wave form components for both R-wave and T-wave obtained by only one electrode pair. The teachings of this invention become readily apparent when viewing the case of left ventricular hypertrophy of FIG. 1A. One electrode sensor pair identified as lead I must be employed to obtain the largest R-wave component and another electrode pair identified as lead III must be used to determine the largest T-wave amplitude. The stroke volume SV is then derived from the ratio of maximum R-wave component over maximum R-wave component. Thus it can be seen, if only one electrode pair such as lead I is employed a negative stroke volume would result because of the negative T-wave amplitude. Alternatively, if only one electrode pair such as lead III (left ventricular hypertrophy) would be employed the stroke volume would be zero as because of the absence of the R-wave component in this lead. As previously mentioned, the stroke volume of an individual is the amount of blood pumped by the individual's heart in one heartbeat.

Figure 4:
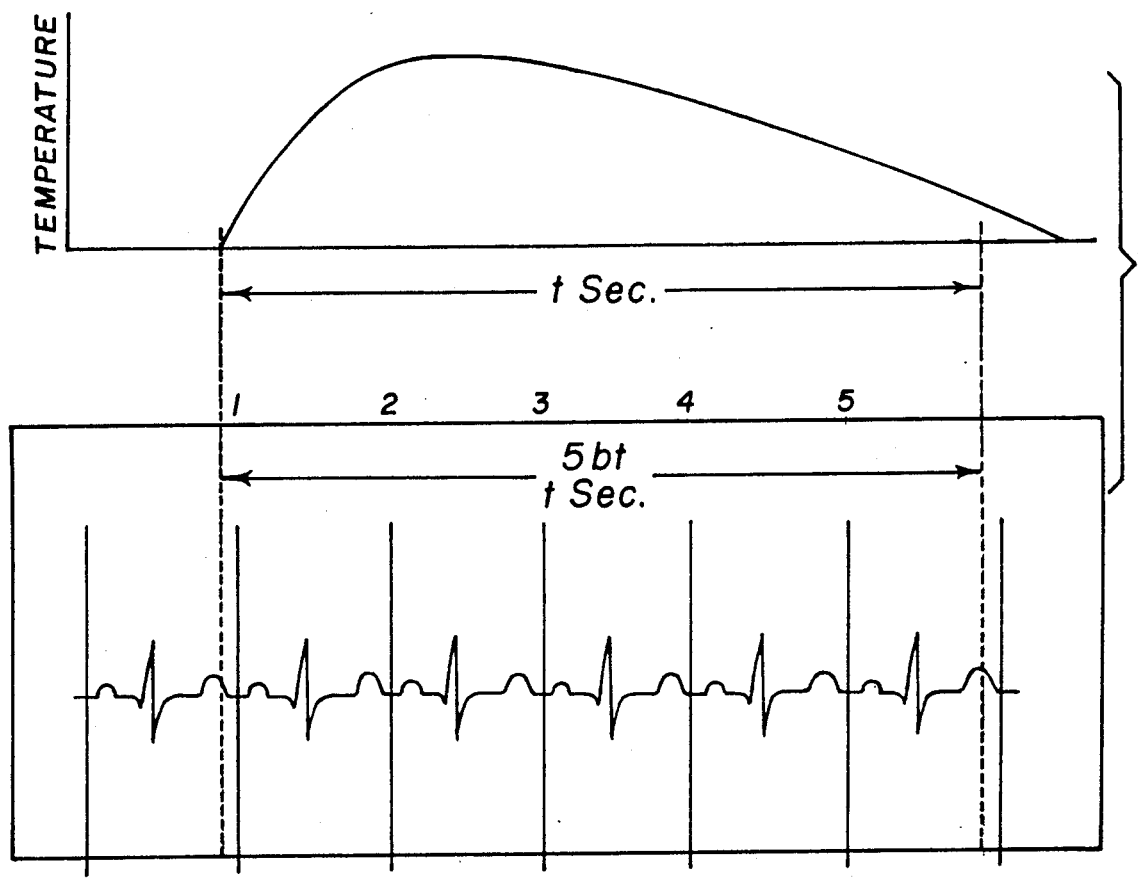
FIG. 4 is a graphical representation stroke volume measurement derived from the prior art thermodilution method.

This relationship may also be shown by utilizing data measured during practice of the previously mentioned thermodilution and dye method. Referring now to FIG. 4, there is illustrated a plot of typical temperature change of an individual's heart subsequent to the injection of a cold fluid into the bloodstream. By measuring the time T required for the temperature of the heart to recover, the cardiac output for this period of time may be accurately calculated. By dividing this value by the number of heartbeats (as measured by an electrocardiogram), the stroke volume of the individual's heart may be calculated. The stroke volume calculated in this manner similarly correlates with the R/T wave ratio using the maximum component wave forms.

Figure 5:
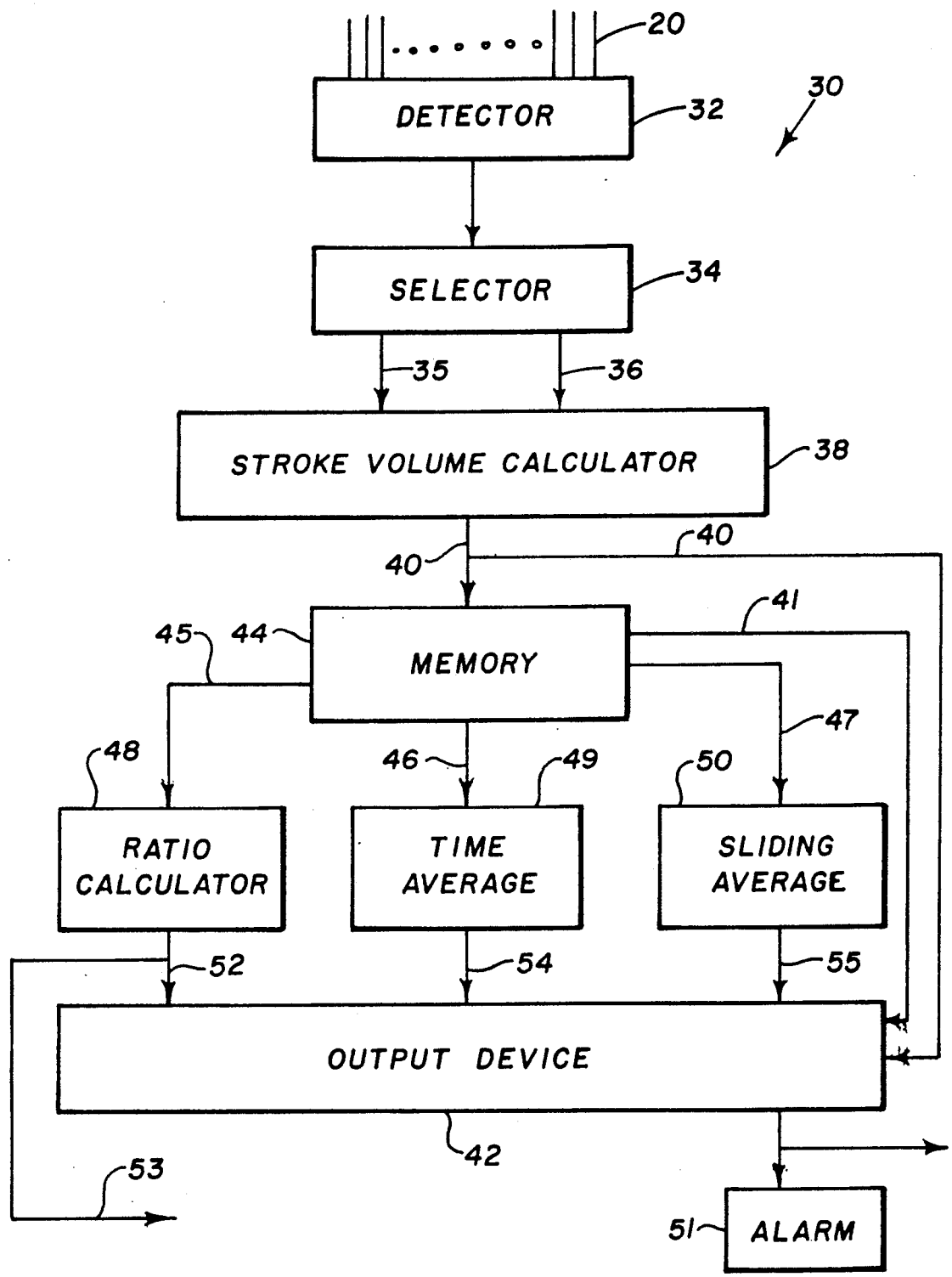
FIG. 5 is a block diagram of a preferred arrangement of apparatus to determine stroke volume and output display according to the present invention

Illustrated in the embodiment of FIG. 5, is a block diagram of the cardiac performance monitoring apparatus of the present invention. Monitoring apparatus functions to calculate the stroke volume of the heart of an individual when supplied with data concerning the plurality of electrocardiographic waveforms of the individual at least two waveforms produced simultaneously must be analyzed although a more accurate determination of stroke volume will be obtained in using multi-leads preferably all twelve of the standard electrocardiographic waveforms. Electrocardiogram leads 20 are electrically connected to detector 32. Detector 32 functions to measure the amplitudes of the R-wave and the T-wave components of each waveform measured by each of the leads 20 all measured amplitudes of the R and T-wave forms are passed to a selector circuit 34 where the waveform having a T-wave with the greatest amplitude and the R-wave with the greatest amplitudes are selected and signals are generated on lines 35 and 36 indicative of the magnitude of waveform 10 which is greatest of all the 14 and T-wave amplitudes 15 respectively.

Lines 35 and 36 coupled to stroke volume calculator 38 wherein the ratio of the selected maximum amplitude of the R-wave to the selected maximum amplitude of the T-wave is calculated for use in arriving at a stroke volume signal according to the equation:

$$SV = 6*R/T + 26.0$$

where SV is the stroke volume;
6 and 26.0 are constants; and
R/T is the ratio of maximum valves of R and T components of electrocardiographic waveforms. The stroke value signal is applied by line 40 to an output device 42 and to a memory device 44.

Output device 42 may be comprised of an alphanumeric display of light emitting diodes, a line printer, or any other conventional interface apparatus.

The stroke volume calculator calculates the stroke volume of the individual according to the previously-mentioned equation which is a regression equation. Memory device 44 allows long-term storage of each of the stroke volume values, and allows later display of these values on output device 42 by connection of memory device through line 41. Memory 44 is used to store stroke volume signals determined at multiple intensity of time. The plurality of stroke volume signals are outputs from memory 44 by lines 45, 46, and 47 to ratio calculator 48, time average calculating 49 and sliding average calculator 50, respectively. In the preferred embodiment, the device includes alarm means 51 in order to generate an alarm in the event that any of the values of the calculated stroke volume differs from desired values.

The ratio calculator 48 utilizes stroke volume values derived from memory 44 for calculating the ratio of a stroke volume value taken during exercise when compared to a stroke volume taken at rest. The ratio is output from the ratio calculator by line 52 as an input to the output device 42 and by a branch line 53 which will be utilizes for other purposes, preferably according to the present invention, during oxygen inhalation and cardiovascular rehabilitation. Such a utilization of the stroke volume ratio will be described in greater detail hereinafter. Time average calculator 49 utilizes stroke volume calculations derived from memory 44 to provide an average stroke volume signal formed by the addition of a number of stroke volume values and the sum thereof divided by the number of stroke volume values which occur in a predetermined time interval. The average stroke signal derived from the time average calculator is delivered by line 54 to output device 42 for display or utilization as discussed above. Lastly, stroke volume signals derived from memory 44 are utilized in the sliding average calculator 50 by averaging stroke volume values taken over a predetermined number of heart beats and updating the average stroke volume values through deleting the earliest occurring stroke volume value and adding a newest occurring stroke volume value to the average calculation. In this way, updated stroke volume average values are produced which are delivered by line 55 to output device 42 for display and other utilization purposes.

Figure 6:
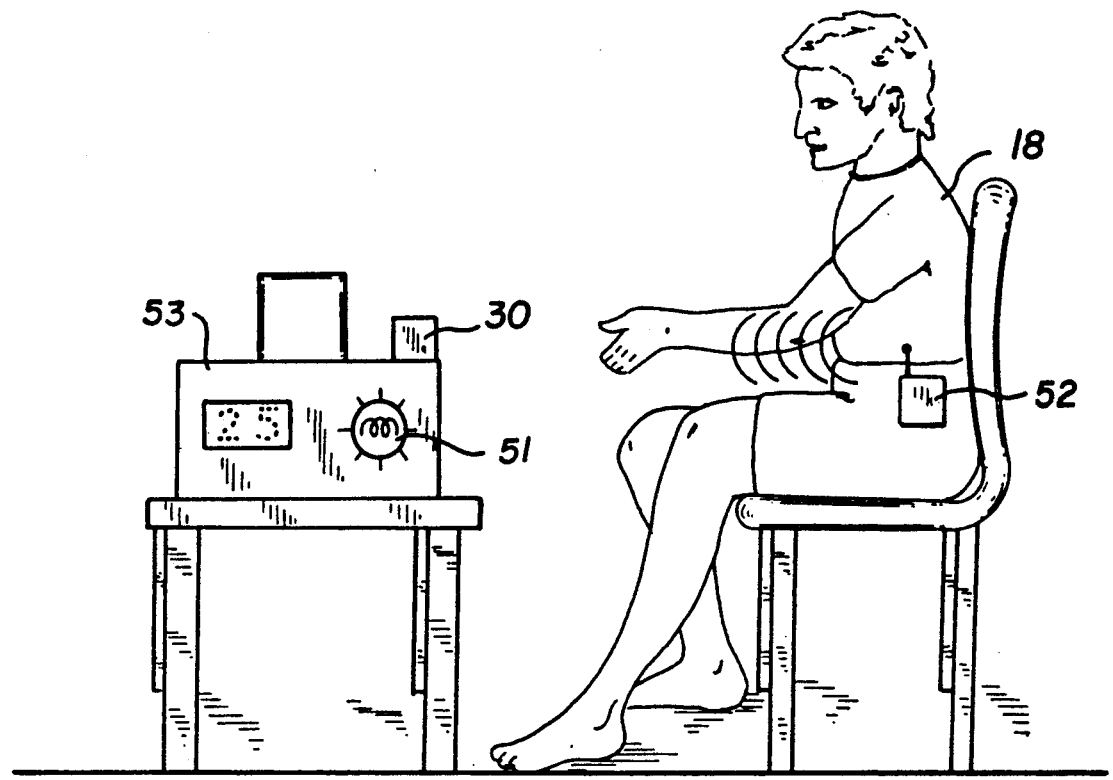
FIG. 6 is a schematic illustration of a remote monitoring system using stroke volume signal according to the present invention.

Referring now to the schematic illustration of FIG. 6, there is illustrated a further embodiment of the instant invention. In this embodiment, the signals needed by the cardiac performance monitoring device 30 to function are supplied by transmitter means 52 to receiver means 53. Receiver 53 is connected to the cardiac monitoring device 30 to supply electrocardiographic signals to the detector device 32 of the apparatus 30 to allow remote monitoring of the cardiac functions of an individual. The monitoring system for this purpose may be positioned at the patient's bedside or at a remote location, for example, a central nurse's station. The cardiac monitoring system contains an alarm 51 to be activated in the event that the stroke volume differs from desired preset values.

In the embodiment of FIG. 6, the apparatus 30 may, for example, be utilized to monitor an individual during postoperative care, and during therapeutic management. In similar manner, monitoring may be adapted to function as an alarm device to generate alarms during sleep irregularities, such as sleep apnea. The stroke volume data serves particularly well in cardiac performance monitoring to provide a quantitative evaluation of the cardiac pumping performance of an individual. This quantitative information concerning the individual is virtually instantaneously, and importantly continuously, all of which is of particular utility because the monitoring device allows calculation of the stroke volume of an individual during the performance of medical procedures, such as open heart surgery, and other times at which prior art devices were incapable of functioning. The apparatus of the present invention further allows the effects of various procedures, such as induction of anesthesia, sternotomy, dissection, going-on bypass, and returning from bypass to be quantitatively measured and analyzed.

Figure 7:
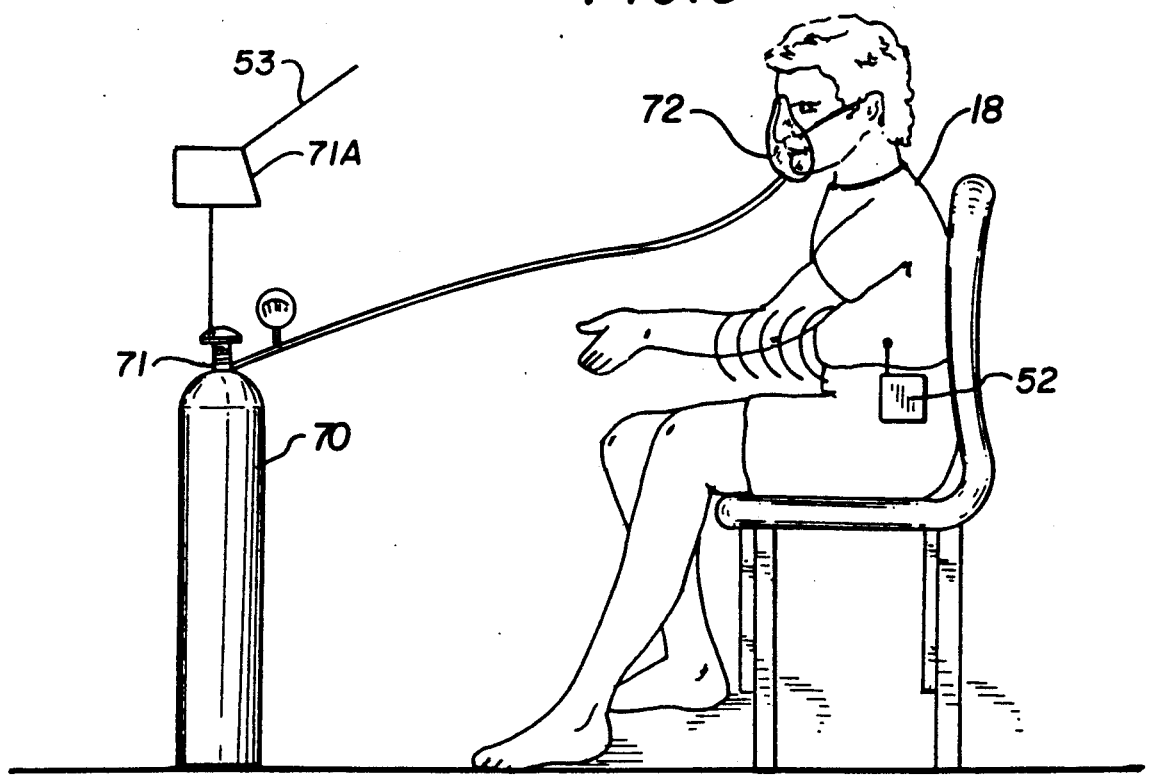
FIG. 7 is a schematic illustration of monitoring system for an individual in a cardiovascular rehabilitation program.

Still further, stroke volume monitoring may be utilized to monitor the individual during oxygen inhalation and cardiovascular rehabilitation programs, such as an oxykinetic exercise program. Referring to the schematic illustration of FIG. 7, the cardiac performance monitoring apparatus 30 shown in FIG. 5 is useful together with transmitter 52 in order to monitor the individual during such exercise. The individual is supplied an oxygen-air mixture from tank 70 through mask 72. The supply of oxygen from tank 70 is regulated by operation of value 71. Such operation can be manually operated by, but preferably by a controller 71A, which is responsive to the stroke volume signal in line 53. The individual then engages in intermittent periods of exercise, the intensity and duration of such exercise being controlled by the magnitude of the individual's stroke volume calculated by the apparatus 30 illustrated in FIG. 5. Oxykinetic programs such as this aid in the improvement in cardiopulmonary performance to progressively elevate the maximum oxygen consumption of the individual 18, in some instances by as much as ten percent. Used in this manner, stroke volume data is also utilized as a safety device to prevent overexertion of the individual during performance of cardiopulmonary rehabilitation programs.

Figure 8B:
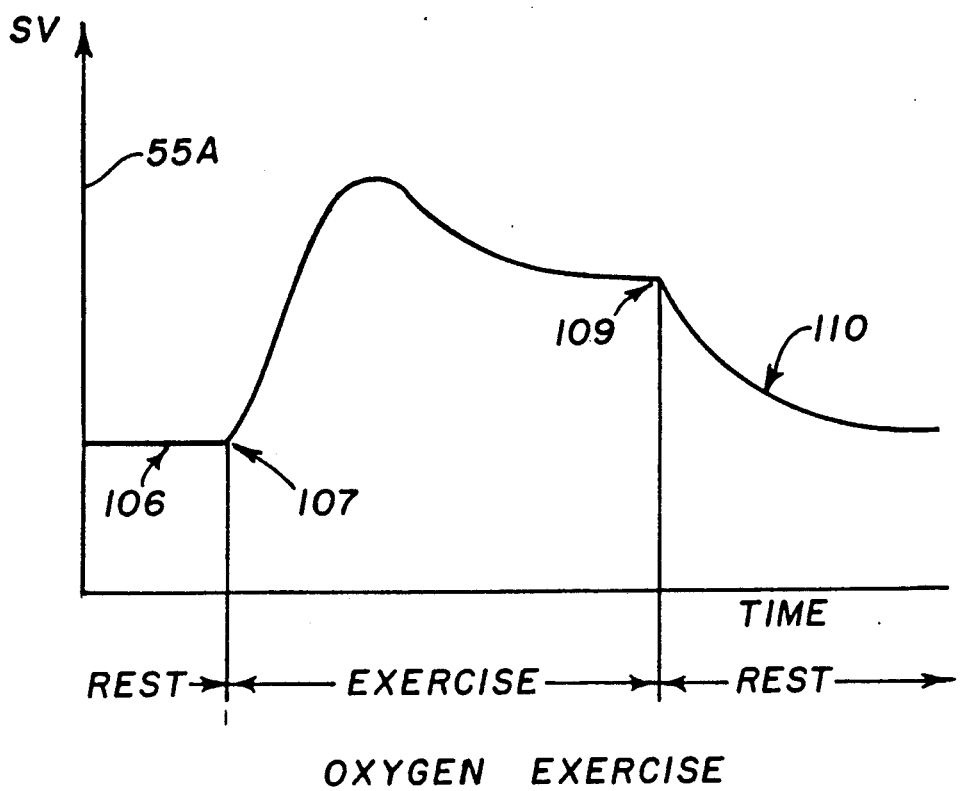
FIGS. 8A and 8B are graphs showing the use of stroke volume data according to the present invention to design and monitor an oxykinetic cardiovascular rehabilitation program comprising oxygen inhalation or oxygen enriched air inhalation with exercise.
Figure 8A:
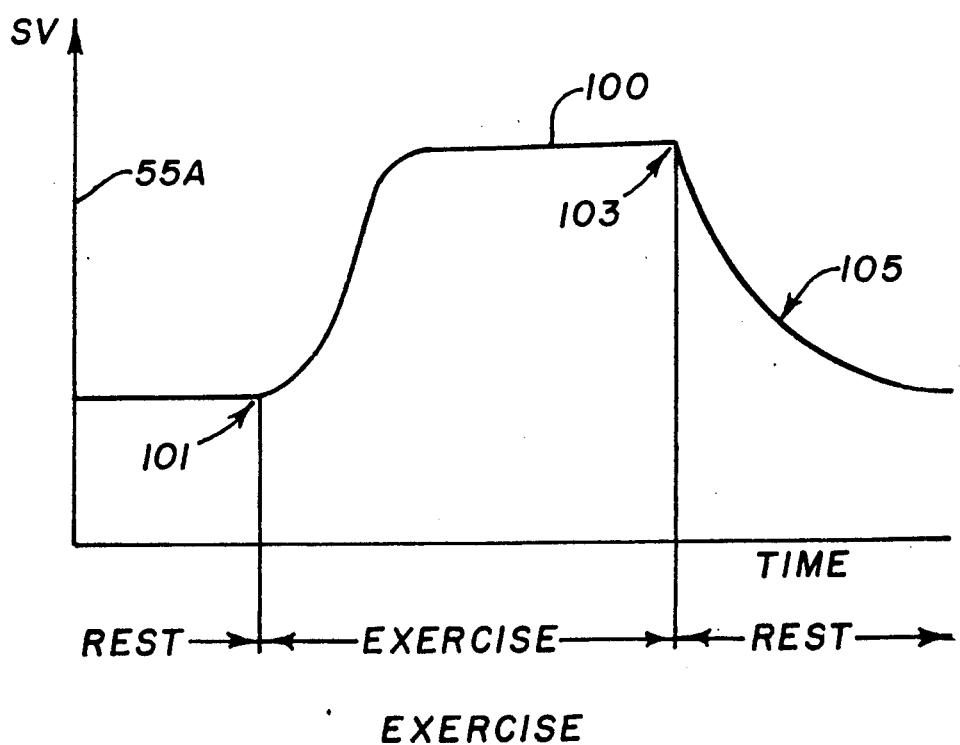

In FIGS. 8A and 8B the graph lines thereof demonstrate typically changes to cardiac pumping as measured by stroke volume of an individual under different circumstances. In both figures the abscissa is time and the ordinate axis 55A is stroke volume. In FIG. 8A graph line segment 100 depicts a stroke volume of an individual at rest whereupon, beginning at a point in time identified by reference numeral 101, the individual undergoes exercise. During the exercise period it can be seen that the stroke volume increases to a maximum value and remains constant for a period of time until exercise terminates as indicated at a point of time identified by reference numeral 103. After termination of exercise, the stroke volume reduces in value as indicated by graph line segment 105. By way of contrast, in FIG. 8B where medication, namely, oxygen enriched air is administered to the individual, the stroke volume is initially determined at a value indicated by graph line segment 106 during which period oxygen enriched air would also be supplied to the individual. Commencement of exercise at point of time identified by reference numeral 107 brings about a increase to the stroke volume to a point in time where the stroke volume reaches a maximum value and thereafter actually reduces to a significantly lower value throughout the period of exercise. Termination of exercise occurs at a point in time identified by reference numeral 109. Thereafter the stroke volume reduces as indicated by graph line segment 110. By comparing these two graph lines it can be seen that the administering of the oxygen enriched air serves to reduce the demand for cardiac performance during exercise. The present invention is also particularly useful in such a program which may consists of repetitive exercise bouts during oxygen inhalation. The information provided by the stroke volume data is especially useful for controlling the duration of intensity of exercise by the individual because of the ability to continuously and almost instantaneously monitor the cardiac stroke volume performance by the individual.

While the present invention has been described in connection with the preferred embodiments of the various figures, it is to be understood that other similar embodiments may be used or modifications and additions may be made to the described embodiment for performing the same function of the present invention without deviating therefrom. Therefore, the present invention should not be limited to any single embodiment, but rather construed in breadth and scope in accordance with the recitation of the appended claims.

What is claimed is:

1. A non-invasive cardiac monitoring device for determining cardiac pumping performance of an individual, comprising, means for generating a plurality of electrocardiogram signals indicative of a plurality electrocardiogram waveforms;

means for detecting the amplitude of a R-wave electrocardiogram component having the greatest amplitude from the plurality of the electrocardiogram signals;

means for detecting the amplitude of a T-wave electrocardiogram component having the greatest amplitude from the plurality of electrocardiogram signals;

means responsive to each of the means for detecting for producing a stroke volume signal which is a function of the ratio of the greatest amplitude of the R-wave component to the greatest amplitude of the T-wave component; and means for displaying values of the stroke volume signal.

2. The non-invasive cardiac monitoring device of claim 1 wherein said stroke volume calculating means generates the stroke volume signal according to the equation:

stroke volume = 6*R/T + 26.0 wherein R/T = the value of the ratio signal generated by the ratio calculating means.

3. A non-invasive cardiac monitoring device according to claim 2 wherein said stroke volume calculating means includes means for generating a signal for monitoring said individual in a cardiac pulmonary rehabilitation program.

4. A non-invasive cardiac monitoring device according to claim 3 further including means responsive to said electrocardiogram sensing means for supplying oxygen enriched air to an individual while exercising in a cardiac pulmonary rehabilitation program.

5. A method to diagnose cardiac performance of an individual, the method including the steps of:

using electrocardiogram sensors on the individual for producing a plurality of electrocardiogram signals corresponding to electrocardiogram waveforms;

selecting a T-wave signal corresponding to the amplitude of the T-wave component having the greatest magnitude from the plurality of electrocardiogram signals;

selecting a R-wave signal corresponding to the amplitude of the R-wave component having the greatest magnitude from the plurality of electrocardiogram signals; and calculating a value of stroke volume as a function of the ratio of the signals of the selected r-wave component to the selected T-wave component.

6. The method of claim 6 including the further step of calculating a value of cardiac output by summing successive values of stroke volume over a period of time.

7. The method according to claim 5 including the further step of using said stroke volume to generate a signal for a cardiac pulmonary rehabilitation program.

8. The method according to claim 7 including the further step of supplying oxygen enriched air to an individual while said individual is exercising to carry-out a cardiac pulmonary rehabilitation program.

9. A method for monitoring the cardiac performance of an individual in a cardiac pulmonary rehabilitation program comprising the steps of:

using electrocardiogram sensors on the individual for producing a plurality of electrocardiogram signals corresponding to electrocardiogram waveforms;

selecting a T-wave signal corresponding to the amplitude of the T-wave component having the greatest magnitude from the plurality of electrocardiogram signals;

selecting a R-wave signal corresponding to the amplitude of the R-wave component having the greatest magnitude from the plurality of electrocardiogram signals;

calculating a value of stroke volume as a function of the ratio of the signals of the selected R-wave component to the selected T-wave component; and using said value of stroke volume to generate a signal for monitoring a cardiac pulmonary rehabilitation program for said individual.

10. The method according to claim 9 wherein said step of using said value of stroke volume includes controlling a supply of medication to said individual.

11. The method according to claim 10 wherein said supply of medication includes oxygen enriched air.

12. A non-invasive cardiac monitoring device for determining cardiac pumping performance of an individual, said device comprising:

means for generating a plurality of electrocardiogram signals indicative of a plurality electrocardiogram waveforms;

means for detecting the amplitude of a R-wave electrocardiogram component having the greatest amplitude from the plurality of the electrocardiogram signals;

means for detecting the amplitude of a T-wave electrocardiogram component having the greatest amplitude from the plurality of electrocardiogram signals;

means responsive to each of the means for detecting for producing a stroke volume signal which is a function of the ratio of the greatest amplitude of the R-wave component to the greatest amplitude of the T-wave component;

means for displaying values of the stroke volume signal; and means for determining a value of cardiac output by summing successive values of stroke volume over a period of time.

13. A method for monitoring the cardiac performance of an individual in a cardiac pulmonary rehabilitation program comprising the steps of:

using electrocardiogram sensors on the individual for producing a plurality of electrocardiogram signals corresponding to electrocardiogram waveforms;

selecting a T-wave signal corresponding to the amplitude of the T-wave component having the greatest magnitude from the plurality of electrocardiogram signals;

selecting a R-wave signal corresponding to the amplitude of the R-wave component having the greatest magnitude from the plurality of electrocardiogram signals;

calculating a value of stroke volume as a function of the ratio of the signals of the selected R-wave component to the selected T-wave component;

using said value of stroke volume including controlling a supply of medication to said individual for monitoring a cardiac pulmonary rehabilitation program for said individual; and controlling the intensity of exercise performed by said individual during said cardiac pulmonary rehabilitation program.

* * * * *